United States Patent
Komori et al.

(10) Patent No.: US 8,558,176 B2
(45) Date of Patent: Oct. 15, 2013

(54) MEDICAL IMAGE DIAGNOSIS APPARATUS AND IMAGE RECONSTRUCTION METHOD

(75) Inventors: Tomoyasu Komori, Otawara (JP); Nobutoku Motomura, Nasushiobara (JP); Takuzo Takayama, Utsunomiya (JP); Atsushi Fukano, Otawara (JP); Masao Yamahana, Nasushiobara (JP); Tatsuya Watanabe, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 105 days.

(21) Appl. No.: 13/152,696

(22) Filed: Jun. 3, 2011

(65) Prior Publication Data
US 2011/0297834 A1    Dec. 8, 2011

(30) Foreign Application Priority Data
Jun. 3, 2010   (JP) ................................ 2010-128227

(51) Int. Cl.
*G01T 1/00*    (2006.01)
(52) U.S. Cl.
USPC ................. 250/336.1; 250/369; 250/363.03; 250/395

(58) Field of Classification Search
USPC ..................... 250/363.03, 336.1, 395; 378/19
See application file for complete search history.

(56) References Cited

U.S. PATENT DOCUMENTS

| | | | | |
|---|---|---|---|---|
| 5,070,455 A | * | 12/1991 | Singer et al. | 378/6 |
| 6,825,930 B2 | * | 11/2004 | Cronin et al. | 356/328 |
| 2007/0096028 A1 | * | 5/2007 | Tanaka | 250/363.07 |

FOREIGN PATENT DOCUMENTS

JP    2007-107995    4/2007

* cited by examiner

*Primary Examiner* — David Porta
*Assistant Examiner* — Abra Fein
(74) *Attorney, Agent, or Firm* — Oblon, Spivak, McClelland, Maier & Neustadt, L.L.P.

(57) ABSTRACT

In a nuclear medicine imaging apparatus as a medical image diagnosis apparatus according to one embodiment, a PET detector is configured to detect a gamma ray emitted from a nuclide introduced into a body of a subject. A PET image reconstruction unit is configured to reconstruct a nuclear medicine image (PET image) as a medical image from the gamma ray projection data created based on the gamma ray detected by the PET detector using successive approximation. A controller is configured to control the PET image reconstruction unit to change the parameter used in the successive approximation depending on information regarding the scanning region in the body of the subject.

9 Claims, 9 Drawing Sheets

| SCANNING REGION | SUBSET NUMBER | ITERATION NUMBER |
|---|---|---|
| 16 TO 17 | 14 | 2 |
| 10 TO 15 | 14 | 4 |
| 1 TO 9 | 14 | 2 |

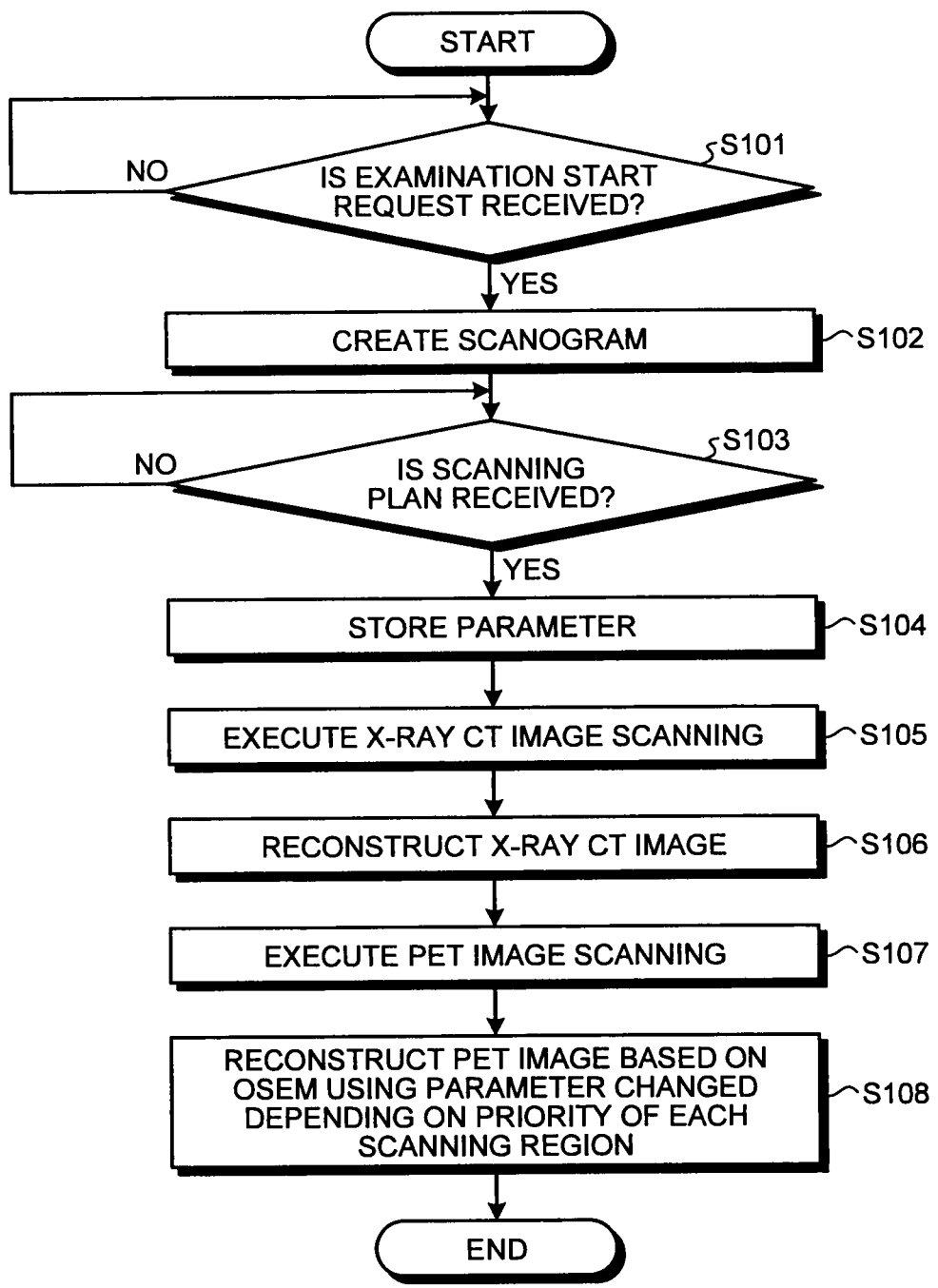

| | SUBSET NUMBER | ITERATION NUMBER |
|---|---|---|
| COUNT RATE >ThU | 14 | 4 |
| COUNT RATE ≤ThU | 14 | 2 |

|            | SUBSET NUMBER | ITERATION NUMBER |
|------------|---------------|------------------|
| AREA >ThA  | 14            | 4                |
| AREA ≤ThA  | 14            | 2                |

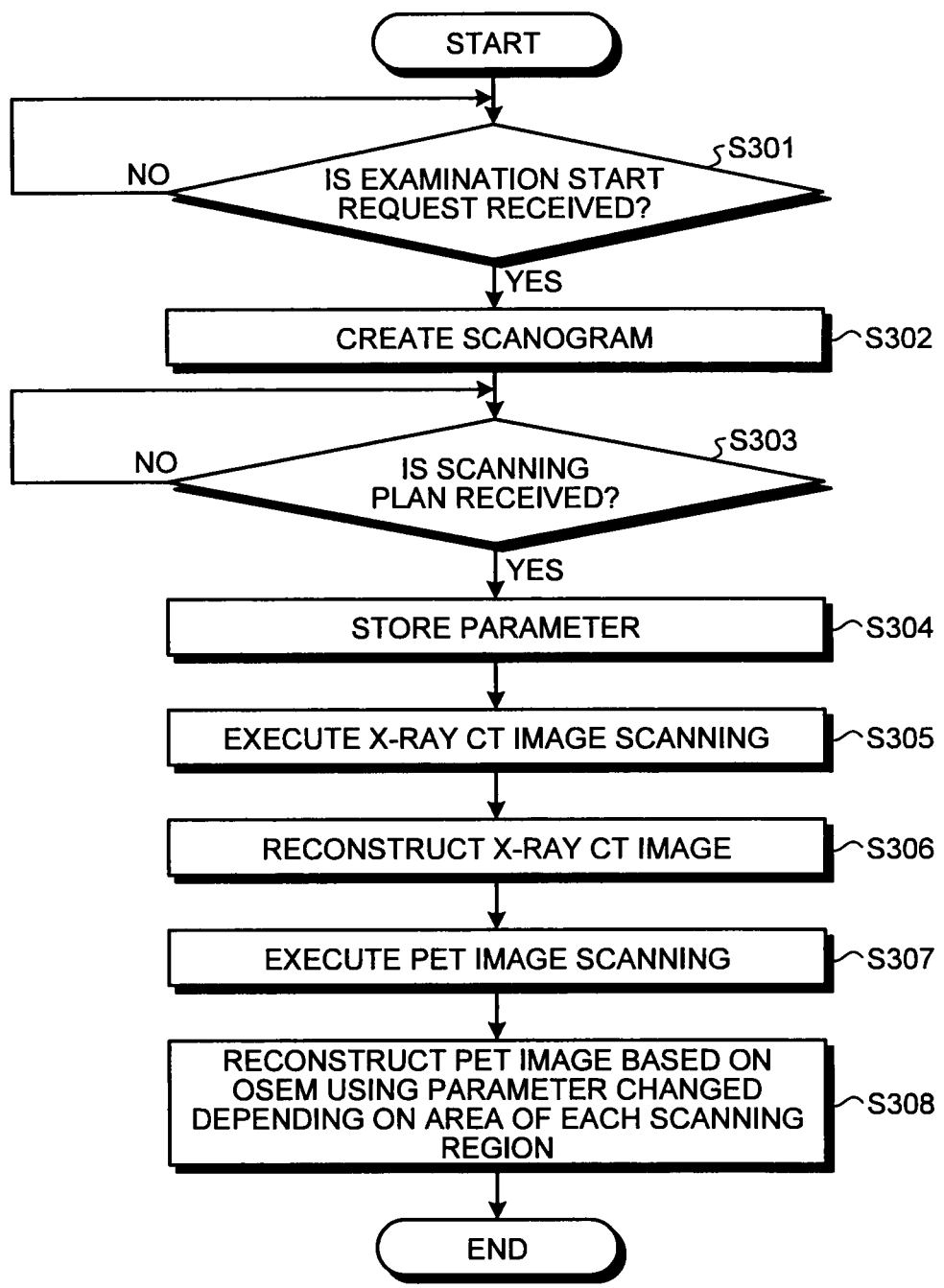

MEDICAL IMAGE DIAGNOSIS APPARATUS AND IMAGE RECONSTRUCTION METHOD

CROSS-REFERENCE TO RELATED APPLICATIONS

This application is based upon and claims the benefit of priority from Japanese Patent Application No. 2010-128227, filed on Jun. 3, 2010; the entire contents of which are incorporated herein by reference.

FIELD

Embodiments described herein relate generally to a medical image diagnosis apparatus and an image reconstruction method.

BACKGROUND

In the related art, nuclear medicine imaging apparatuses such as a single photon emission computed tomography (SPECT) apparatus or a positron emission computed tomography (PET) apparatus have been known as a medical image diagnosis apparatus capable of performing functional diagnosis in body tissues of a subject.

Specifically, the nuclear medicine imaging apparatus detects a gamma ray emitted from an isotope or a labeled compound selectively received in the body tissues using a detector and reconstructs a nuclear medicine image obtained by portraying a radiation dose distribution of the detected gamma ray.

In recent years, apparatuses such as a PET-CT apparatus or SPECT-CT apparatus are widely used, in which a nuclear medicine imaging apparatus is integrated with an X-ray computed tomography (X-ray CT) apparatus that provides shape information in the body tissues of the subject. For example, a whole-body examination using the PET-CT apparatus is indispensable in tumor diagnosis.

In the SPECT apparatus or the PET apparatus, typically, a successive approximation type image reconstruction method is used unlike an image reconstruction method performed in the X-ray CT apparatus. The successive approximation method is not an analytical method, but highly tolerant to noise in principle. As an example of the successive approximation methods, a maximum likelihood expectation maximization (MLEM) technique and an ordered subset MLEM (OSEM) technique, in which an MLEM algorithm is modified to remarkably reduce a processing time, have been developed.

However, since the image reconstruction method based on the successive approximation takes a long time, examination efficiency using the medical images may be degraded.

BRIEF DESCRIPTION OF THE DRAWINGS

FIG. 7 is a flowchart illustrating processing in the PET-CT apparatus according to the first embodiment;

FIG. 11 is a flowchart illustrating processing in the PET-CT apparatus according to the third embodiment.

DETAILED DESCRIPTION

According to one embodiment, a medical image diagnosis apparatus includes a detector, an image reconstruction unit, and a controller. The detector is configured to detect a radioactive ray. The image reconstruction unit is configured to reconstruct a medical image from projection data created based on the radioactive ray detected by the detector using successive approximation. The controller is configured to control the image reconstruction unit to change a parameter used in the successive approximation depending on information regarding a scanning region in a body of a subject.

Hereinafter, embodiments of the medical image diagnosis apparatus will be described in detail with reference to the accompanying drawings. In the following description, a PET-CT apparatus obtained by integrating a positron emission computed tomography (PET) apparatus which is a nuclear medicine imaging apparatus with an X-ray computed tomography (CT) apparatus will be described as an example of the medical image diagnosis apparatus.

Figure 1:
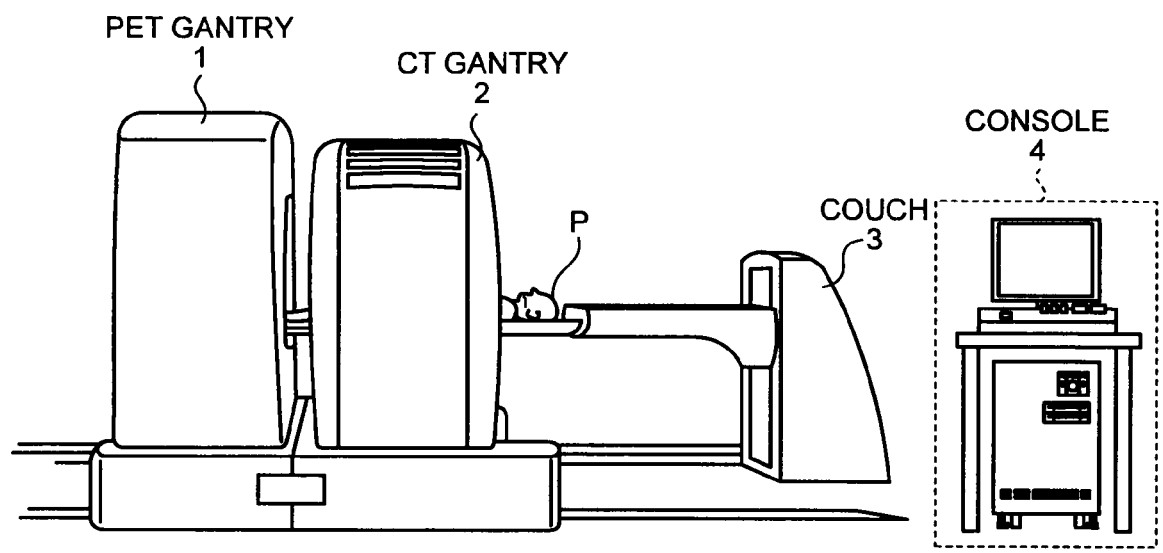
FIG. 1 is a diagram illustrating the overall structure of a PET-CT apparatus according to a first embodiment.

First, an overall configuration of the PET-CT apparatus according to a first embodiment will be described with reference to FIG. 1. FIG. 1 is a diagram illustrating an overall configuration of the PET-CT apparatus according to the first embodiment.

As shown in FIG. 1, the PET-CT apparatus according to the first embodiment includes a PET gantry 1, a CT gantry 2, a couch 3, and a console 4.

Figure 2A:
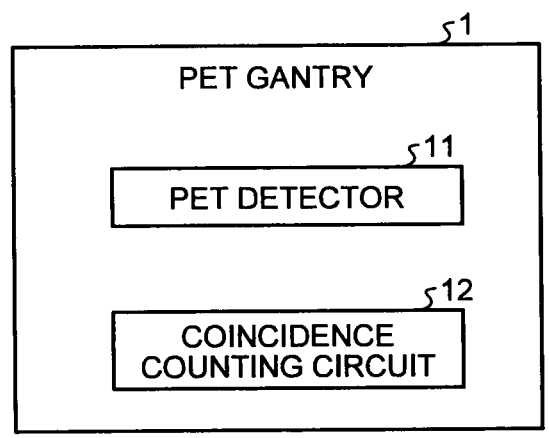
FIGS. 2A and 2B are diagrams illustrating a configuration of the PET gantry.
Figure 2B:
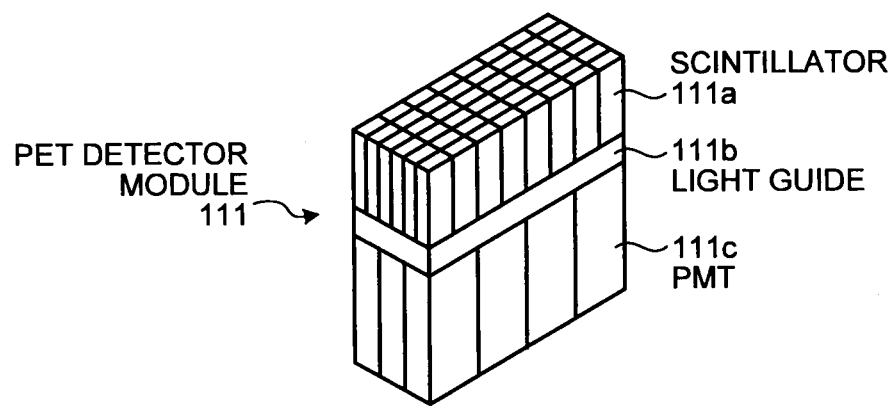

The PET gantry 1 is an apparatus for creating gamma ray projection data for reconstructing a PET image by detecting a pair of gamma rays emitted from the body tissues that have received positron emission nuclides introduced into the body of the subject P. FIGS. 2A and 2B are diagrams illustrating a configuration of the PET gantry.

As shown in FIG. 2A, the PET gantry 1 includes a PET detector 11, a coincidence counting circuit 12, and the like. The PET detector 11 is a photon counting type detector for detecting the gamma ray emitted from the body of the subject P. Specifically, the PET detector 11 includes a plurality of PET detector modules 111 arranged to surround the circumference of the body of the subject P in a ring shape.

For example, as shown in FIG. 2B, the PET detector module 111 is an anger type detector having a scintillator 111$a$, a photomultiplier tube (PMT) 111$c$, and a light guide 111$b$.

In the scintillator 111$a$, a plurality of scintillation crystals such as NaI or BGO that converts incident the gamma ray emitted from a body of a subject P into visible light are arranged in 2-dimensional space as shown in FIG. 2B. In addition, the photomultiplier tube 111$c$ is an apparatus that multiplies the visible light outputted from the scintillator 111$a$ and converts the visible light into an electric signal. As shown in FIG. 2B, a plurality of photomultiplier tubes 111$c$ are densely arranged by interposing the light guides 111$b$. The light guide 111$b$ is used to transmit the visible light outputted from the scintillator 111a to the photomultiplier tube 111c and is made of a plastic material or the like having high light transmittance.

The photomultiplier tube 111c includes a photocathode that receives the scintillation light and generates photoelectrons, a multi-stage dynode that generates an electric field for accelerating the generated photoelectrons, and an anode which is an outlet through which electrons flow out. The electron emitted from the photocathode by the photoelectric effect is accelerated to the dynode and collides with the surface of the dynode so that a plurality of electrons are ejected. If such a phenomenon is repeated over the multi-stage dynodes, the number of electrons is multiplied like an avalanche so that the number of electrons at the anode reaches about 1,000,000 electrons. In such an example, the gain of the photomultiplier tube 111c increases up to 1,000,000. In addition, typically, a voltage of 1000 V or higher is applied between the dynode and the anode in order to obtain amplification using the avalanche phenomenon.

As such, the PET detector module 111 counts the number of gamma rays emitted from the body of the subject P by converting the gamma rays into visible light using the scintillator 111a and converting the converted visible light into the electric signal using the photomultiplier tube 111c.

The coincidence counting circuit 12 shown in FIG. 2A is connected to each of a plurality of photomultiplier tubes 111c provided in each of a plurality of PET detector module 111. In addition, the coincidence counting circuit 12 creates coincidence counting information for determining an incident direction of a pair of gamma rays emitted from the positron based on the output result of the PET detector module 111. Specifically, the coincidence counting circuit 12 determines the incident position of the gamma ray (the position of the scintillator 111a) by computing a gravity center position based on the position of the photomultiplier tube 111c, that converts the visible light outputted from the scintillator 111a into an electric signal at the same timing and outputs it, and the strength of the electric signal. In addition, the coincidence counting circuit 12 computes an energy value of the incident gamma ray by computing (integral and differentiation) the strength of the electric signal outputted from each photomultiplier tube 111c.

In addition, the coincidence counting circuit 12 searches the output result of the PET detector 11 to find a combination corresponding to an incident timing (time) of the gamma ray within a certain time window width and an energy value within a certain energy window width (coincidence finding). For example, as a search condition, the time window width may be set to 2 nsec, and the energy window width may be set to 350 to 550 keV. In addition, the coincidence counting circuit 12 creates coincidence counting information (coincidence list) by using the output result of the found combination as information obtained by coincidentally counting two disappeared photons. In addition, the coincidence counting circuit 12 transmits the coincidence counting information as gamma ray projection data for the PET image reconstruction to the console 4 shown in FIG. 1. In addition, a line connecting two detection positions obtained by coincidentally counting two disappeared photons is called a line of response (LOR). Alternatively, the coincidence counting information may be created in the console 4.

Figure 3:
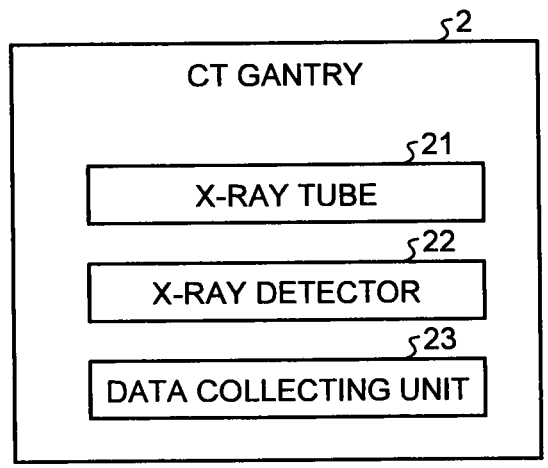
FIG. 3 is a diagram illustrating a configuration of the CT gantry.

Returning to FIG. 1, the CT gantry 2 is an apparatus for creating X-ray projection data for reconstructing X-ray CT image or X-ray projection data for creating scanogram by detecting the X-ray transmitting through the body of the subject P. FIG. 3 is a diagram illustrating a configuration of the CT gantry.

As shown in FIG. 3, the CT gantry 2 includes an X-ray tube 21, an X-ray detector 22, a data collecting unit 23, and the like. The X-ray tube 21 generates X-ray beams and irradiates the generated X-ray beams to the body of the subject P. The X-ray detector 22 is an apparatus for detecting the X-ray transmitting through the body of the subject P at the position opposite to the X-ray tube 21. Specifically, the X-ray detector 22 is a two-dimensional array type detector for detecting two-dimensional strength distribution data of the X-ray transmitting through the body of the subject P. More specifically, in the X-ray detector 22, a plurality of detection element lines including X-ray detection elements corresponding to a plurality of channels are arranged along the body-axis direction of the subject P. In addition, the X-ray tube and the X-ray detector are supported by a rotatable frame (not shown) inside the CT gantry 2.

The data collecting unit 23 as a data acquisition system (DAS) performs an amplification process, an analog-to-digital (A/D) conversion process, or the like for the two-dimensional X-ray strength distribution data detected by the X-ray detector 22 to create X-ray projection data. In addition, the data collecting unit 23 transmits the X-ray projection data to the console 4 of FIG. 1.

Returning to FIG. 1, the couch 3 is a bed for loading the body of the subject P. The couch 3 is sequentially moved to respective scanning bores of the CT gantry 2 and the PET gantry 1 based on the instruction from the PET-CT apparatus operator through the console 4.

That is, the PET-CT apparatus initially scans the X-ray CT image and then scans the PET image by moving the couch 3. For example, the PET-CT apparatus scans the X-ray CT image through a helical scanning that helically scans the scanning region in the body of the subject P using X-rays by moving the couch 3 while rotating the rotatable frame of the CT gantry 2. In addition, the PET-CT apparatus scans the PET image by moving the couch 3 such that the scanning region in the body of the subject P is inserted into the scanning bore of the PET gantry 1.

In the examination using the PET-CT apparatus, a scanogram is obtained by scanning the whole body of the subject P along the body-axis direction by moving the couch 3 while the X-ray is irradiated from the X-ray tube 21 with the rotatable frame being fixed. The scanogram of the body of the subject P is referenced by an operator who establishes a scanning plan for the X-ray CT images and the PET images.

Figure 4:
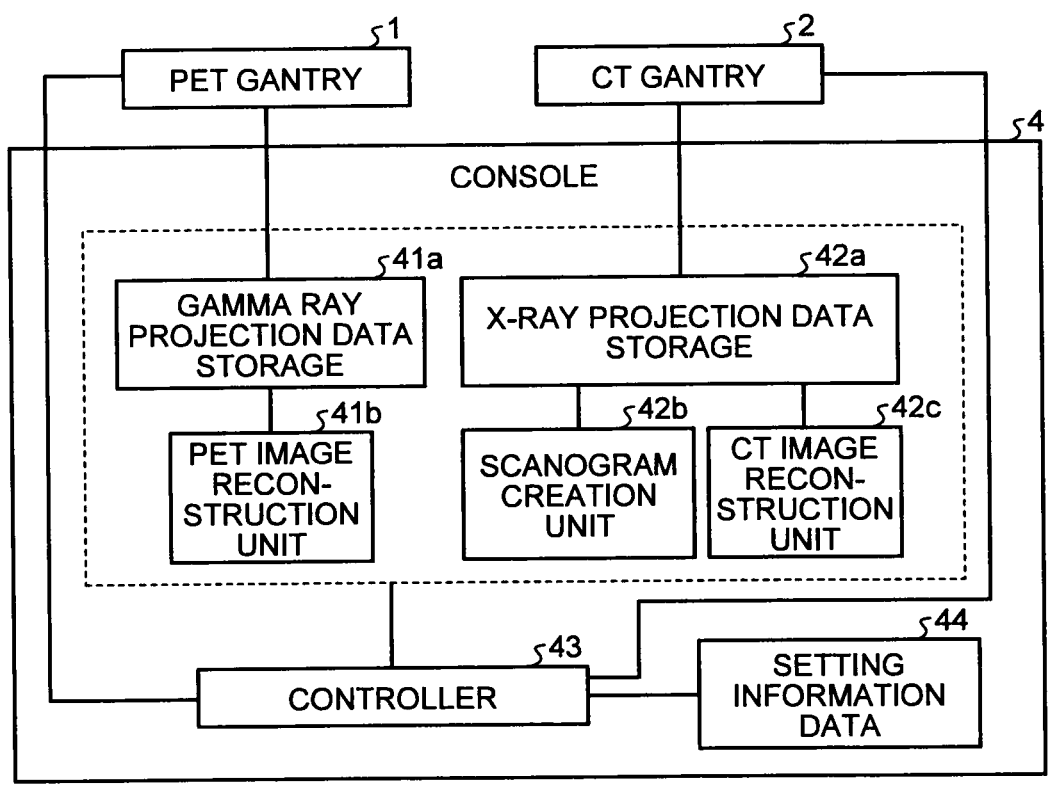
FIG. 4 is a diagram illustrating a configuration of the console.

The console 4 is an apparatus for receiving instructions from an operator and controlling the scanning process in the PET-CT apparatus. FIG. 4 is a diagram illustrating a configuration of the console.

As shown in FIG. 4, the console 4 includes a gamma ray projection data storage 41a, a PET image reconstruction unit 41b, an X-ray projection data storage 42a, a scanogram creation unit 42b, and a CT image reconstruction unit 42c. Furthermore, as shown in FIG. 4, the console 4 includes a controller 43 and a setting information data 44.

The X-ray projection data storage 42a stores the X-ray projection data transmitted from the data collector 23. Specifically, the X-ray projection data storage 42a stores X-ray projection data for creating the scanogram and X-ray projection data for reconstructing the X-ray CT images.

The scanogram creation unit 42b creates a scanogram from the X-ray projection data for creating the scanogram stored in the X-ray projection data storage 42a. The CT image reconstruction unit 42c reconstructs the X-ray CT image by performing back-projection, for example, based on a filtered back projection (FBP) method, for the reconstruction X-ray projection data stored in the X-ray projection data storage 42a.

That is, the scanogram creation unit 42b creates a scanogram for establishing a scanning plan for the whole-body examination using the PET-CT apparatus. In addition, the CT image reconstruction unit 42c reconstructs a plurality of X-ray CT images obtained by scanning a plurality of cross-sections perpendicular to the body-axis direction of the subject P from the X-ray projection data based on an scanning condition (such as a slice width) determined by the scanning plan for the whole-body examination using the PET-CT apparatus.

The gamma ray projection data storage 41a stores the gamma ray projection data transmitted from the coincidence counting circuit 12. The PET image reconstruction unit 41b reconstructs the PET images from the gamma ray projection data stored in the gamma ray projection data storage 41a using successive approximation.

Hereinafter, the successive approximation in the PET image reconstruction unit 41b will be described. As an example of the successive approximation, there are known a maximum likelihood expectation maximization (MLEM) and an ordered subset MLEM (OSEM) in which the MLEM algorithm is modified to remarkably reduce a processing time.

According to the MLEM, the PET image is reconstructed as an initial image, for example, through a back-projection process such as the FBP from the gamma ray projection data collected in practice. In addition, estimated projection data 1 are created by performing a projection process for the initial image, and the estimated projection data 1 are processed by the back-projection to obtain a reconstruction image 1. In addition, estimated projection data 2 are created by performing a projection process for the reconstruction image 1, and a reconstruction image 2 is reconstructed by performing the back-projection process for the estimated projection data 2. Such a process is repeated as many as a repeated computation number in the successive approximation. In the following description, the repeated computation number is referred to as an iteration number.

As a result, the estimated projection data are created with a ratio between the projection data collected in practice and the estimated projection data being set to about "1." The reconstruction image obtained by performing back-projection for the estimated projection data corresponds to a PET image representing the most probable cumulative distribution of the positron emission nuclides.

In addition, a general equation used in the reconstruction of the MLEM can be expressed as follows:

$$x_j^{(n+1)} = \frac{x_j^{(n)}}{\sum_{j=1}^{I} a_{ij}} \sum_{i=1}^{I} a_{ij} \frac{y_i}{\sum_{k=1}^{J} a_{ik} x_k^{(n)}} \quad (1)$$

where, "$X_j$" denotes an average of the number of photons emitted from pixels j (j=1 to J), "$y_i$" denotes the number of photons detected by $LOR_i$ (i=1 to I), n (n=1, 2, . . . ) denotes the iteration number, and "$a_{ij}$" denotes a detection characteristic of the PET apparatus and is called a system matrix. In other words, Equation 1 means that correction is made such that a ratio between the measurement data "$y_i$" and the estimated projection data "$\Sigma_k a_{ik} x_k^{(n)}$" obtained from the image by computation is approximated to "1."

In addition, in the OSEM, the gamma ray projection data are divided into some subsets, and the aforementioned successive approximation is performed for each subset to correct images. That is, the OSEM of which the subset number is set to "1" is the MLEM.

Here, a total computation number of the PET image reconstruction unit 41b depends on the iteration number when the MLEM is executed. In addition, the total computation number of the PET image reconstruction unit 41b depends on the subset number multiplied by the iteration number when the OSEM is executed.

Hereinafter, description will be made for a case where the PET image reconstruction unit 41b reconstructs the PET image based on the OSEM. However, the first embodiment described herein may be applied to a case where the PET image reconstruction unit 41b reconstructs the PET image based on the MLEM.

The controller 43 controls the overall processing in the PEC-CT apparatus. Specifically, the controller 43 controls scanning of the PET-CT apparatus by controlling the PET gantry 1 and the CT gantry 2. In addition, the controller 43 controls the processing in the PET image reconstruction unit 41b using the data stored in the gamma ray projection data storage 41a. In addition, the controller 43 controls the processing in the scanogram creation unit 42b and the CT image reconstruction unit 42c using the data stored in the X-ray projection data storage 42a. In addition, the controller 43 receives instructions of an operator from an input/output device (not shown). In addition, the controller 43 performs control to display a graphical user interface (GUI) for allowing an operation to enter instructions, a scanogram, an X-ray CT image, and a PET image on the input/output device. For example, the PET image reconstruction unit 41b, the scanogram creation unit 42b, the CT image reconstruction unit 42c, and the controller 43 is implemented by an integrated circuit, such as an application specific integrated circuit (ASIC) or a field programmable gate array (FPGA), or an electronic circuit, such as a central processing unit (CPU) or a micro processing unit (MPU).

The setting information data 44 is a storage, which stores the data used when the controller 43 controls the PET image reconstruction unit 41b. In addition, the setting information data 44 will be described in detail below.

Hereinbefore, the overall configuration of the PET-CT apparatus has been described according to the first embodiment. The PET-CT apparatus having such a configuration according to the first embodiment reconstructs the PET as a nuclear medicine image from the gamma ray projection data created from the gamma rays detected by the PET detector 11 based on the successive approximation.

For example, the PET-CT apparatus according to the first embodiment executes whole-body scanning for the X-ray CT image using a helical scan after obtaining the scanogram in order to perform a whole-body examination of the subject P. Here, the scanning of the physical body of the subject P is completed, for example, within several tens seconds through high-speed helical scanning accompanied by high-speed rotation of the rotatable frame and multiple lines of the X-ray detectors 22. In addition, for the reconstruction time of the X-ray CT images, several hundreds to several thousands X-ray CT images can be reconstructed nearly in real time immediately after the scanning.

However, the whole-body scanning for the PET image takes 10 to 20 or more minutes in order to measure the gamma rays at each scanning region by moving couch 3 to each scanning region. Furthermore, the reconstruction for the PET images based on the successive approximation sometimes takes several minutes to several tens minutes or more after the last scanning region is scanned. According to the MLEM, the iteration number serves as an important parameter for determining image quality and reconstruction time. For example, in the event of the whole-body examination, if an optimal iteration number is set to obtain best image quality, the reconstruction time for the PET images increases. That is, in the event of the examination using PET images, if image quality is preferred in all scanning regions, the time required for reconstruction increases. Therefore, examination efficiency is degraded.

In this regard, the PET-CT apparatus according to the first embodiment performs control in the controller 43 as described below in detail.

The controller 43 controls the PET image reconstruction unit 41b such that parameters (such as the iteration number and the subset number) used in the OSEM can be changed depending on information regarding the scanning region in the body of the subject P. For example, the controller 43 changes parameters used in the OSEM such that a total computation number in the event of the whole-body scanning for the subject P (a sum of "iteration number"×"subset number" for each scanning region) is within a preset range.

Figure 5:
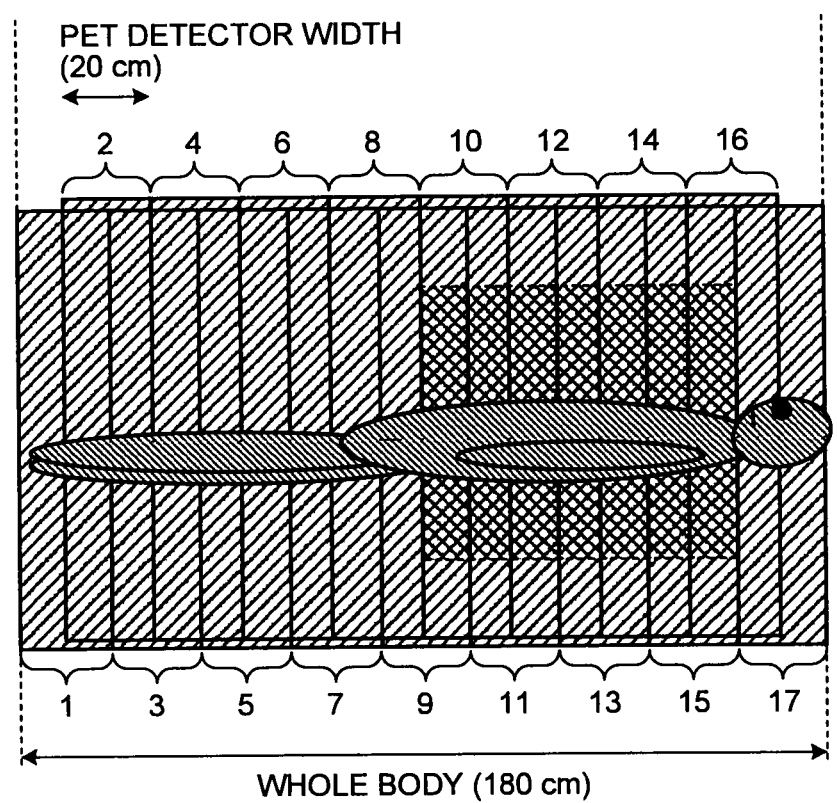
FIG. 5 is a diagram illustrating an example of a PET image capturing plan set using a scanogram.

First, an operator of the PET-CT apparatus sets parameters capable of optimizing and reducing the reconstruction time for the PET image with reference to the scanogram. FIG. 5 is a diagram illustrating an example of the scanning plan for the PET images set using the scanogram.

For example, it is assumed that the subject P is 180 cm in height, and the width of the PET detector 11 along the longitudinal direction of the couch 3 is 20 cm. In this case, for example, as shown in FIG. 5, an operator sets the whole-body examination of the subject P with reference to the scanogram such that a total of 17 PET images are obtained with an interval of 20 cm while the scanning regions are overlapped with each other by 10 cm. That is, an operator performs settings such that the PET images of the scanning regions 1 to 17 are scanned by moving the couch 3 by 10 cm.

Figures 6A, 6B:
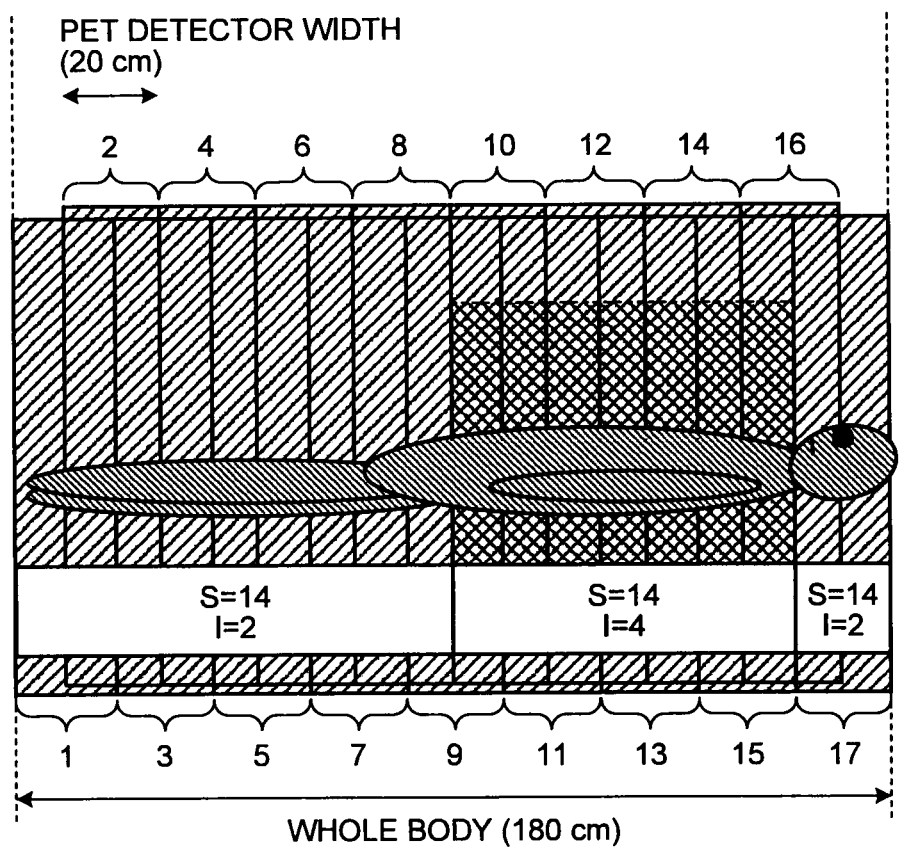
FIGS. 6A and 6B are diagrams illustrating an example of parameter settings.

In addition, an operator performs settings to change parameters depending on priorities of each scanning region as information on the scanning regions. As a result, the setting information data 44 stores the parameters changed depending on the priorities of the scanning regions. FIGS. 6A and 6B are diagrams illustrating an example of the setting information data according to the first embodiment.

For example, in the OSEM performed by the PET image reconstruction unit 41b, it is assumed that the optimal iteration number for obtaining optimal image quality of the PET images is within a range of "4 to 10." In addition, in the OSEM performed by the PET image reconstruction unit 41b, it is assumed that the minimum iteration number allowing the image quality of the PET images to be used in diagnosis is set to "2."

In this case, as shown in FIG. 6A, an operator sets the parameters for the scanning regions 10 to 15 corresponding to a chest region and an abdominal region desired to perform image diagnosis in detail using the PET images to "subset number: 14, iteration number: 4." In addition, as shown in FIG. 6A, an operator sets the parameters for the scanning regions 16 and 17 corresponding to a head region determined not to perform image diagnosis in detail using the PET images to "subset number: 14, iteration number: 2." In addition, as shown in FIG. 6A, an operator sets the parameters for the scanning regions 1 to 9 corresponding to a lumbar region and a lower extremity region determined not to perform image diagnosis in detail using the PET images to "subset number: 14, iteration number: 2."

As a result, as shown in FIG. 6B, the setting information data 44 stores the parameters for the scanning regions 16 and 17 having a low priority as "subset number: 14, iteration number: 2." In addition, as shown in FIG. 6B, the setting information data 44 stores the parameters for the scanning regions 10 to 15 having a high priority as "subset number: 14, iteration number: 4." In addition, as shown in FIG. 6B, the setting information data 44 stores the parameters of the scanning regions 1 to 9 having a low priority as "subset number: 14, iteration number: 2."

The controller 43 acquires the parameters corresponding to the scanning region in the body of the subject P from the setting information data 44 and controls the reconstruction process in the PET image reconstruction unit 41b.

As a result, the PET image reconstruction unit 41b reconstructs the PET images based on the OSEM using the subset number and the iteration number set for each scanning region from the gamma ray projection data for each scanning region.

In addition, the parameters for each scanning region may be set manually by an operator as described above, or may be set automatically by the controller 43. In this case, for example, the controller 43 automatically sets the parameters of each scanning region by automatically determining the ranges corresponding to a head region, a chest region, an abdominal region, a lumbar region, and a lower extremity region from the measurement result for the body of the subject P and the scanogram.

In the foregoing first embodiment, description has been made for a case where the parameters are set using the scanogram. However, in the first embodiment, for example, information on the regions of the body of the subject P inserted into the scanning bore of the PET gantry 1 may be previously acquired from the measurement result for the body of the subject P depending on the position of the couch 3 without using the scanogram, so that the parameters may be set corresponding to the position of the couch 3.

However, when the healing effect for a tumor is diagnosed in a tumor examination using the PET image, the PET examination for the healing portion (such as a liver) may be repeated to examine a tumor size. Even in this case, while the whole-body examination is performed in order not to lose a change to find metastasis, the iteration number for the healing portion is preferably optimized to precisely reconstruct the PET image of the healing portion. For this reason, the scanogram is preferably used in order to precisely determine the healing portion.

Next, processing in a PET-CT apparatus according to the first embodiment will be described with reference to FIG. 7. FIG. 7 is a flowchart illustrating processing in the PET-CT apparatus according to the first embodiment.

As shown in FIG. 7, the PET-CT apparatus according to the first embodiment determines whether or not the examination start request is received from an operator (step S101). Here, if it is determined that the examination start request is not received (NO in step S101), the PET-CT apparatus is in a standby state. Otherwise, if it is determined that the examination start request is received (YES in step S101), the scanogram scanning is executed, and the scanogram creation unit 42b creates the scanogram (step S102).

In addition, the controller 43 determines whether or not the scanning plan including parameter settings is received from an operator who references the scanogram (step S103). Here, if it is determined that the scanning plan including the parameter settings is not received (NO in step S103), the PET-CT apparatus is in a standby state. Otherwise, if it is determined that the scanning plan including the parameter settings is received (YES in step S103), the controller 43 stores the parameter settings in the setting information data 44 (step S104). In addition, the parameters stored in step S104 are changed depending on the priority of the scanning region as shown in FIG. 6A.

The controller 43 controls the CT gantry 2 to execute the X-ray CT image scanning (step S105), and the CT image reconstruction unit 42c reconstructs the X-ray CT images (step S106). Then, the controller 43 controls the PET gantry 1 to execute the PET image scanning (step S107).

The PET image reconstruction unit 41b reconstructs the PET images under control of the controller 43 with reference to the setting information data 44 based on the OSEM using the parameters changed depending on the priority of each scanning region (step S108), and the process is terminated.

As described above, in the first embodiment, the PET detector 11 detects the gamma ray emitted from the nuclide introduced into the body of the subject P. The PET image reconstruction unit 41b reconstructs the nuclear medicine images (PET image) from the gamma ray projection data created based on the gamma rays detected by the PET detector 11 using the successive approximation. The controller 43 controls the PET image reconstruction unit 41b to change the parameters (the iteration number and the subset number) used in the successive approximation depending on the information regarding the scanning regions of the body of the subject P.

Therefore, in the first embodiment, for example, it is possible to dynamically change the parameters used in the successive approximation for each scanning region such that the reconstruction time of the PET image reconstruction unit 41b is within a predetermined range. That is, in the first embodiment, it is possible to reduce the time required in the PET examination by dynamically changing the parameters used in the successive approximation for each scanning region. As a result, in the first embodiment, it is possible to improve examination efficiency using the nuclear medicine image (PET image).

In addition, in the first embodiment, the setting information data 44 stores the parameters changed depending on the priority of the scanning region in the body of the subject P as information regarding the scanning region in the body of the subject P. In addition, the controller 43 acquires the parameters corresponding to the scanning region in the body of the subject P from the setting information data 44 and controls the image reconstruction process in the PET image reconstruction unit 41b.

Therefore, in the first embodiment, it is possible to perform settings such that image quality is preferred for the scanning region having a high priority in the image diagnosis, while the reconstruction time is preferred for the scanning region having a low priority in the image diagnosis. As a result, in the first embodiment, for example, it is possible to perform settings such that the reconstruction time is preferred for a lumbar region including a bladder or a head region at which a false-positive signal is highly probably exhibited, while the image quality is preferred for the abdominal region as a healing portion. As a result, in the first embodiment, it is possible to improve the examination efficiency using the nuclear medicine image (PET image) in response to the request from a radiologist.

Figures 8, 9:
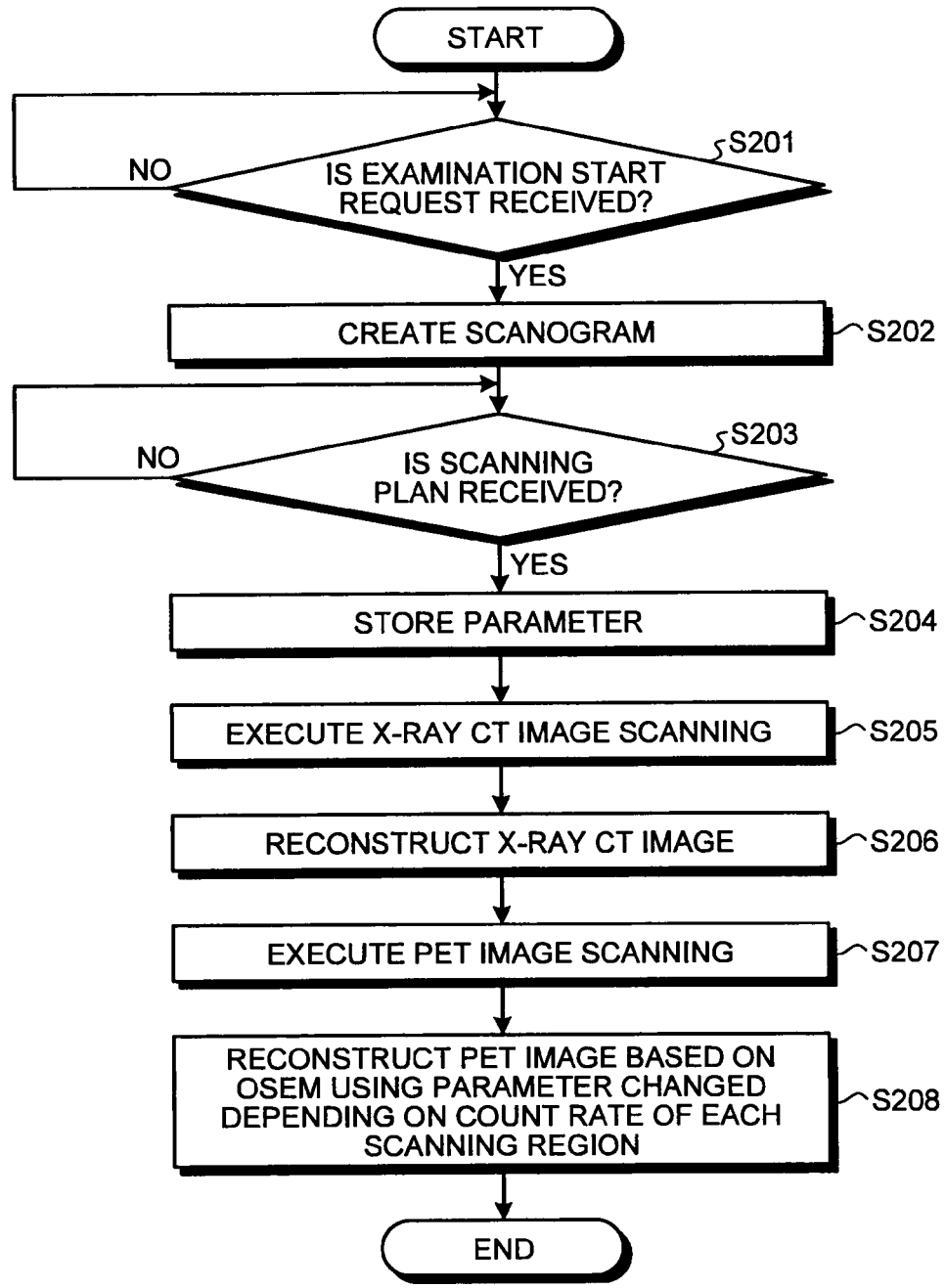
FIG. 8 is a diagram illustrating setting information data according to a second embodiment.
FIG. 9 is a flowchart illustrating processing in the PET-CT apparatus according to the second embodiment.

In the second embodiment, a case where the parameters used in the successive approximation are changed depending on the information acquired in the event of PET image scanning will be described with reference to FIG. 8. In addition, FIG. 8 is a diagram illustrating setting information data according to the second embodiment.

Although the console 4 of the PET-CT apparatus according to the second embodiment is configured similar to the console 4 of the PET-CT apparatus according to the first embodiment that has been described with reference to FIG. 4, the contents stored in the setting information data 44 used by the controller 43 in the event of parameter change is different from those of the first embodiment.

The controller 43 according to the second embodiment performs a parameter change process based on the counting result for the gamma ray detected by the PET detector 11 as information regarding the scanning region in the body of the subject P. Specifically, in the second embodiment, first, parameters for the overall scanning regions are set to initial values. For example, in the second embodiment, parameters for the overall scanning regions are set to "subset number: 14, iteration number: 2."

In the second embodiment, for example, a threshold value ThU is set for the number count (count rate) regarding how frequent the PET detector 11 detects light per unit time. In addition, in the second embodiment, the scanning region having a count rate equal to or lower than the threshold value ThU is set to perform the reconstruction process using the initial settings "subset number: 14, iteration number: 2." In addition, in the second embodiment, for example, the scanning region having a count rate higher than the threshold value ThU is set to perform the reconstruction process by changing the iteration number to an optimal value.

Through such settings, the setting information data 44 according to the second embodiment stores the parameter having a count rate higher than the threshold value ThU as "subset number: 14, iteration number: 4" as shown in FIG. 8. In addition, the setting information data 44 stores the parameter having a count rate equal to or lower than the threshold value ThU as "subset number: 14, iteration number: 2" as shown in FIG. 8.

In addition, the controller 43 computes the count rate, for example, by counting the number of outputs of the PET detector 11 for each scanning region in the event of the PET image scanning. In addition, the controller 43 compares the computed count rate and the threshold value and determines the parameter based on the comparison result. In addition, the controller 43 transmits the determined parameter to the PET image reconstruction unit 41b. As a result, the PET image reconstruction unit 41b reconstructs the PET images for each scanning region using the parameters based on the count rate.

In the foregoing description, a case where the count rate is used as a count result has been exemplified. However, the second embodiment may be modified such that a change rate of the number count may be used as the count result.

Next, the processing in the PET-CT apparatus according to the second embodiment will be described with reference to FIG. 9. FIG. 9 is a flowchart illustrating processing in the PET-CT apparatus according to the second embodiment.

As shown in FIG. 9, the PET-CT apparatus according to the second embodiment determines whether or not the examination start request is received from an operator (step S201). Here, if it is determined that the examination start request is not received (NO in step S201), the PET-CT apparatus is in a standby state. Otherwise, if it is determined that the examination start request is received (YES in step S201), the scanogram scanning is executed, and the scanogram creation unit 42b creates the scanogram (step S202).

In addition, the controller 43 determines whether or not the scanning plan including parameter settings is received from an operator who references the scanogram (step S203). Here, if it is determined that the scanning plan including parameter settings is not received (NO in step S203), the PET-CT apparatus is in a standby state. Otherwise, if it is determined that the scanning plan including parameter settings is received (YES in step S203), the controller 43 stores the parameter settings in the setting information data 44 (step S204). In addition, the parameters stored in step S204 are the parameters changed depending on the count rate for the scanning region as shown in FIG. 8.

In addition, the controller 43 controls the CT gantry 2 to execute the X-ray CT image scanning (step S205), and the CT image reconstruction unit 42c reconstructs the X-ray CT image (step S206). Then, the controller 43 controls the PET gantry 1 to execute the PET image scanning (step S207).

The PET image reconstruction unit 41b reconstructs the PET images under control of the controller 43 with reference to the setting information data 44 based on the OSEM using the parameters changed depending on the count rate for each scanning region (step S208), and the process is terminated. The data stored in the setting information data 44 may be stored either in the event of the examination start request or before the examination start request.

As described above, in the second embodiment, the controller 43 performs the parameter change process based on the count result of the gamma rays detected by the PET detector 11 as information regarding the scanning region in the body of the subject P. Therefore, in the second embodiment, the image reconstruction giving higher preference to image quality can be performed for the scanning region having high probability to find a portion at which the gamma ray detection probability increases (for example, a tumor) in the PET images. In addition, in the second embodiment, the image reconstruction giving higher preference to reconstruction time can be performed for the scanning region determined not to be important in the image diagnosis due to low probability of detecting the gamma rays.

Figures 10A, 10B:
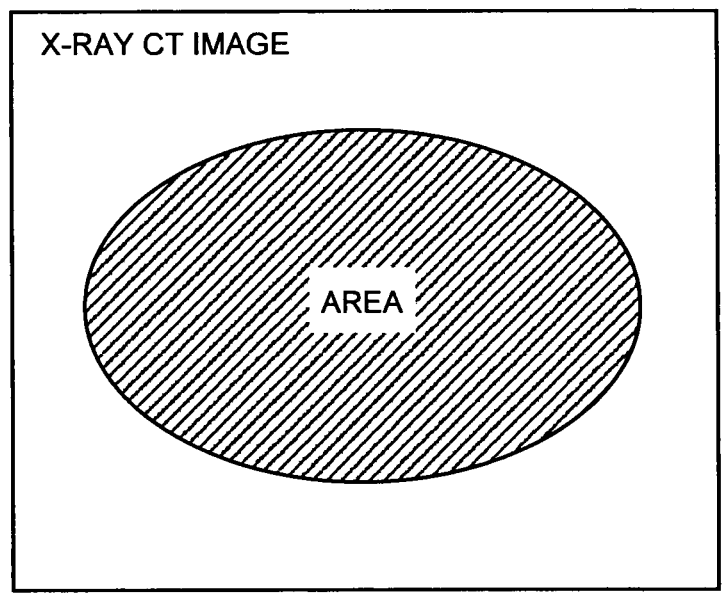
FIGS. 10A and 10B are diagrams illustrating setting information data according to a third embodiment.

In the third embodiment, a case where the parameters used in the successive approximation are changed depending on information acquired from the X-ray CT image as a tissue image will be described with reference to FIGS. 10A and 10B. FIGS. 10A and 10B are diagrams illustrating setting information data according to the third embodiment.

Although the console 4 of the PET-CT apparatus according to the third embodiment is configured similar to the console 4 of the PET-CT apparatus according to the first embodiment that has been described with reference to FIG. 4, the contents stored in the setting information data 44 used by the controller 43 in the event of parameter change is different from those of the first and second embodiments.

The controller 43 according to the third embodiment performs a parameter change process based on the size of the body of the subject P included in the X-ray CT image obtained by scanning the body of the subject P as information regarding the scanning region in the body of the subject P. Specifically, in the third embodiment, similar to the second embodiment, first, parameters for all scanning regions are set to an initial value. For example, in the third embodiment, the parameters for all scanning regions are set to "subset number: 14, iteration number: 2."

In the third embodiment, for example, as shown in FIG. 10A, the area of the body of the subject P included in the X-ray CT image obtained by scanning the cross-section within the scanning region of the PET image is set to an index for changing the parameter. In the third embodiment, a threshold value ThA is set for the area. In the third embodiment, for example, the scanning region having an area equal to or smaller than the threshold value ThA is set to perform the reconstruction process using the initial settings "subset number: 14, iteration number: 2." In the third embodiment, for example, the scanning region having an area larger than the threshold value ThA is set to perform the reconstruction process by changing the iteration number to an optimal value.

Through such settings, the setting information data 44 according to the third embodiment stores the parameter having an area larger than the threshold value ThA as "subset number: 14, iteration number: 4" as shown in FIG. 10B. In addition, the setting information data 44 stores the parameter having an area equal to or smaller than the threshold value ThA as "subset number: 14, iteration number: 2" as shown in FIG. 10B.

In addition, the controller 43 acquires the X-ray CT image obtained by scanning the scanning region of the PET image from the CT image reconstruction unit 42c, and computes the area of the body of the subject P included in the acquired X-ray CT image. In addition, the controller 43 compares the computed area and the threshold value and determines the parameter based on the comparison result. In addition, the controller 43 transmits the determined parameter to the PET image reconstruction unit 41b. As a result, the PET image reconstruction unit 41b reconstructs the PET images for each scanning region using the parameter based on the area.

In the foregoing embodiment, description has been made for a case where the area is used as a size for each scanning region in the body of the subject P. However, in the third embodiment, a volume may be used as the size for each scanning region in the body of the subject P. In this case, the setting information data 44 stores information on the parameter based on a magnitude relationship between the volume and the threshold value. In addition, for example, the controller 43 acquires all of the X-ray CT images included in the scanning region 11 of the PET image of FIG. 5 and computes the volume of the body of the subject P included in the scanning region 11 based on the area of the body of the subject P included in each X-ray CT image and a slice width.

Next, processing in the PET-CT apparatus according to the third embodiment will be described with reference to FIG. 11. FIG. 11 is a flowchart illustrating processing in the PET-CT apparatus according to the third embodiment.

As shown in FIG. 11, the PET-CT apparatus according to the third embodiment determines whether or not the examination start request is received from an operator (step S301). Here, if it is determined that the examination start request is not received (NO in step S301), the PET-CT apparatus is in a standby state. Otherwise, if it is determined that the examination start request is received (YES in step S301), the scanogram scanning is executed, and the scanogram creation unit 42b creates the scanogram (step S302).

In addition, the controller 43 determines whether or not the scanning plan including parameter settings is received from an operator who references the scanogram (step S303). Here, if it is determined that the scanning plan including parameter settings is not received (NO in step S303), the PET-CT apparatus is in a standby state. Otherwise, if it is determined that the scanning plan including parameter settings is received (YES in step S303), the controller 43 stores the parameter setting in the setting information data 44 (step S304). In addition, the parameters stored in step S304 are the parameters changed depending on the area of the body of the subject P in the scanning region as shown in FIG. 10B.

In addition, the controller 43 controls the CT gantry 2 to execute the X-ray CT image scanning (step S305), and the CT image reconstruction unit 42c reconstructs the X-ray CT image (step S306). Then, the controller 43 controls the PET gantry 1 to execute the PET image scanning (step S307).

The PET image reconstruction unit 41b reconstructs the PET image under control of the controller 43 with reference to the setting information data 44 based on the OSEM using the parameters changed depending on the area for each scanning region (step S308), and the process is terminated. In addition, the data stored in the setting information data 44 may be stored either in the event of the examination start request or before the examination start request.

As described above, in the third embodiment, the controller 43 performs the parameter change process based on the size of the body of the subject P included in the X-ray CT image obtained by scanning the body of the subject P as information regarding the scanning region in the body of the subject P. Here, the gamma ray is absorbed in the body of the subject P and then detected. That is, in a case where a portion having a large size is scanned, attenuance of the detected gamma ray is high. Therefore, in order to improve image quality, the parameters used in the successive approximation is necessary to be optimized. In this regard, in the third embodiment, the image can be reconstructed by giving high preference to image quality of the scanning region at which the attenuance increases.

While the foregoing description has been made for a case where the size of the body of the subject P is computed using the X-ray CT image, the tissue image as a target for computing the size of the body of the subject P may be an MRI image.

In addition, in the first to third embodiments, description has been made for a case where the PET image reconstruction unit 41b performs the image reconstruction process using the parameters for each scanning region whenever the gamma ray projection data are created. However, in the first to third embodiments, in the event of examination, the PET image reconstruction unit 41b may reconstruct the PET images using the minimum iteration number based on the gamma ray projection data for each scanning region, and the image reconstruction process using the parameters for each scanning region may be performed again when a radiologist reads the images.

In addition, in the first to third embodiments, description has been made for a case where the parameter to be changed is the iteration number. However, the first to third embodiments may be applied to a case where the parameter to be changed is the subset number. That is, the first to third embodiments may be applied to a case where the subset number for each scanning region is changed based on the optimal subset number by which the image quality of the PET image is optimized and the minimum subset number by which image quality of the PET image can be provided for image diagnosis.

In addition, the first to third embodiments described above may be applied to a case where both the iteration number and the subset number are used as the parameter to be changed. However, since a quantitative analysis using the PET images is necessary, it is preferable that only one of the iteration number and the subset number is used as the parameter to be changed.

In addition, in the first to third embodiments, description has been made for a case where the image reconstruction process is performed based on the OSEM. However, the first to third embodiments may be applied to a case where the image reconstruction process is performed based on the MLEM. In this case, iteration number is used as the parameter to be changed.

In addition, in the first to third embodiments, description has been made for a case where the parameter change process is performed in the PET-CT apparatus. However, the first to third embodiments described above may also be applied to a case where the parameter change process is performed in an independent PET apparatus that acquires the X-ray CT image or the scanogram obtained by scanning the body of the subject P using the X-ray CT apparatus.

In addition, the parameter change process for each scanning region described in the first to third embodiments may be applied to a SPECT-CT apparatus or a SPCT apparatus that reconstructs the SPECT images based on the successive approximation.

In addition, the image reconstruction method described above in the first to third embodiments, that is, the parameter change process based on information on the scanning region may be performed for the X-ray CT apparatus. In recent years, an X-ray CT apparatus including a photon-counting type detector (photon counting CT) used in the PET apparatus or the SPECT apparatus is being developed instead of the current mode measurement type detector.

The photon counting CT detects the X-rays transmitting through the body of the subject P using a photo counting type detector. Specifically, the photon counting CT counts the X-ray energy value transmitting through the body of the subject for each detection element using a photon counting type detector. As a result, the photon counting CT can collect spectra allowing for estimation of elements consisting of tissues of the body of the subject as the X-ray projection data. As a result, the photon counting CT can reconstruct the X-ray CT images such that an element level difference is portrayed in detail.

Here, the photon counting CT also tries to perform the X-ray CT image reconstruction based on the successive approximation. However, as described above, since image reconstruction method based on the successive approximation takes a long time, the examination efficiency using the X-ray CT image may be degraded.

In this regard, in order to improve the examination efficiency using the X-ray CT image, the X-racy CT apparatus as the photon counting CT performs the image reconstruction method described above in the first to third embodiments. For example, the X-ray detection detector 22 shown in FIG. 3 is a photon counting type detector for detecting X-rays transmitting through the body of the subject P, and the CT image reconstruction unit 42c shown in FIG. 4 is a processing unit for reconstructing the X-ray CT images based on the successive approximation.

In this case, the controller 43 shown in FIG. 4 controls the CT image reconstruction unit 42c to change the parameters used in the OSEM (iteration number and subset number) or the parameter used in the MLEM (iteration number) depending on information regarding the scanning region in the body of the subject P.

The information regarding the scanning region in the body of the subject P includes, for example, a priority of the scanning region in the body of the subject P as described in the first embodiment. In this case, the controller 43 transmits to the CT image reconstruction unit 42c the parameter(s) set depending on the priority for each scanning region in the body of the subject P for which the whole-body scanning is performed using the CT gantry 2. As a result, the CT image reconstruction unit 42c reconstructs the X-ray CT image based on the successive approximation using the parameters changed depending on the priority of the scanning region in the body of the subject P.

Alternatively, the information regarding the scanning region in the body of the subject P includes, for example, the count result for the X-rays detected by the X-ray detection detector 22 as described in the second embodiment. In this case, the controller 43 computes the count rate, for example, by counting the number of outputs of the X-ray detector 22 for each scanning region in the body of the subject P for which the whole-body scanning is performed using the CT gantry 2. In addition, the controller 43 controls the CT image reconstruction unit 42c to perform the reconstruction process for the scanning region having a count rate equal to or lower than the threshold value, for example, by setting the iteration number to a minimum value. In addition, the controller 43 controls the CT image reconstruction unit 42c to perform the reconstruction process for the scanning region having a count rate higher than the threshold value by changing the iteration number to an optimal iteration number.

Alternatively, the information regarding the scanning region in the body of the subject P includes, for example, a size of the body of the subject P included in the tissue image obtained by scanning the body of the subject P as described in the third embodiment. In this case, the tissue image is, for example, the X-ray CT image as an initial image obtained by reconstructing the X-ray projection data based on the FBP method by executing the successive approximation with the CT image reconstruction unit 42c.

The controller 43 acquires the initial image from the CT image reconstruction unit 42c and computes the area of the body of the subject P included in the acquired initial image. In addition, the controller 43 compares the computed area and the threshold value and determines the parameters based on the comparison result. In addition, the controller 43 controls the CT image reconstruction unit 42c to perform the reconstruction process for the scanning region having an area equal to or smaller than the threshold value, for example, by setting the iteration number to a minimum value. In addition, the controller 43 controls the CT image reconstruction unit 42c to perform the reconstruction process for the scanning region having an area larger than the threshold value by changing the iteration number to an optimal value. For example, the tissue image may be, for example, an MRI image obtained by scanning the body of the subject P using an MRI apparatus.

In the foregoing description, a case where the X-ray CT apparatus as a part of the PET-CT apparatus performs the image reconstruction methods described in the first to third embodiments has been exemplified. However, the image reconstruction methods described in the first to third embodiments may be applied to an independent X-ray CT apparatus.

As described above, according to the first to third embodiments, it is possible to improve the examination efficiency using medical images.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image diagnosis apparatus, comprising:
   a detector configured to detect a radioactive rays;
   an image reconstruction unit configured to reconstruct a medical image from projection data created based on the radioactive rays detected by the detector using successive approximation; and
   a controller configured to set a parameter that is used in the successive approximation and determines reconstruction time and image quality, depending on information regarding a scanning region in a body of a subject,
   wherein the image reconstruction unit is configured to reconstruct the medical image by performing the successive approximation using the parameter set by the controller.

2. The medical image diagnosis apparatus according to claim 1, further comprising:
   a storage that stores, in association with an identifier of the scanning region, a parameter changed and set by an operator,
   wherein the controller is configured to acquire, from the storage based on the identifier of the scanning region, the parameter used in the successive approximation, and to control an image reconstruction process in the image reconstruction unit.

3. The medical image diagnosis apparatus according to claim 1,
   wherein the controller is configured to perform a process of changing the parameter based on a count result of the radioactive rays detected by the detector as the information regarding the scanning region in the body of the subject.

4. The medical image diagnosis apparatus according to claim 1,
   wherein the controller is configured to perform the process of changing the parameter based on a size of the body of the subject as the information regarding the scanning region in the body of the subject, and the size of the body of the subject is the area of the body of the subject included in an X-ray CT image or an MRI image obtained by scanning the scanning region prior to the reconstruction of the medical image.

5. The medical image diagnosis apparatus according to claim 1,
   wherein the parameter includes an iteration number used for the successive approximation.

6. The medical image diagnosis apparatus according to claim 1,
   wherein the parameter includes a subset number and an iteration number used for the successive approximation.

7. The medical image diagnosis apparatus according to claim 1,
   wherein the detector is configured to detect, as the radioactive rays, gamma rays, emitted from a nuclide introduced into the body of the subject, and
   the image reconstruction unit is configured to reconstruct a nuclear medicine image from projection data created based on the gamma rays detected by the detector, using the successive approximation.

8. The medical image diagnosis apparatus according to claim 1,
   wherein the detector is configured to detect X-rays transmitting through the body of the subject as the radioactive rays, and
   the image reconstruction unit is configured to reconstruct an X-ray CT image from projection data created based on the X-rays detected by the detector, using the successive approximation.

9. An image reconstruction method, comprising:
   detecting radioactive rays with a detector;
   reconstructing a medical image from projection data created based on the radioactive rays detected by the detector using successive approximation by an image reconstruction unit; and
   setting a parameter that is used in the successive approximation and determines reconstruction time and image quality, depending on information regarding a scanning region in a body of a subject, wherein the reconstructing step includes reconstructing the medical image by performing the successive approximation using the set parameter.

* * * * *